United States Patent
Miller (10) Patent No.: US 8,728,124 B2
(45) Date of Patent: May 20, 2014

(54) SPINAL ROD EXTENDERS AND METHODS OF USE

(75) Inventor: Keith E Miller, Germantown, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 340 days.

(21) Appl. No.: 13/071,838

(22) Filed: Mar. 25, 2011

(65) Prior Publication Data

US 2011/0172717 A1 Jul. 14, 2011

Related U.S. Application Data

(62) Division of application No. 11/469,008, filed on Aug. 31, 2006, now Pat. No. 7,922,746.

(51) Int. Cl.
*A61B 17/70* (2006.01)
(52) U.S. Cl.
USPC ........... 606/256; 606/250; 606/251; 606/253; 606/259; 606/260
(58) Field of Classification Search
USPC .................................. 606/250–253
See application file for complete search history.

(56) References Cited

U.S. PATENT DOCUMENTS

| | | | | |
|---|---|---|---|---|
| 5,885,284 A * | 3/1999 | Errico et al. | ................... | 606/252 |
| 5,947,965 A * | 9/1999 | Bryan | ................... | 606/86 A |
| 5,980,523 A * | 11/1999 | Jackson | ................... | 606/252 |
| 6,217,578 B1 * | 4/2001 | Crozet et al. | ................... | 606/252 |
| 6,554,832 B2 * | 4/2003 | Shluzas | ................... | 606/252 |
| 2002/0169448 A1 * | 11/2002 | Vanacker | ................... | 606/61 |
| 2003/0114853 A1 * | 6/2003 | Burgess et al. | ................... | 606/61 |
| 2005/0107789 A1 * | 5/2005 | Sweeney | ................... | 606/61 |
| 2005/0228378 A1 * | 10/2005 | Kalfas et al. | ................... | 606/61 |

* cited by examiner

*Primary Examiner* — Nicholas Woodall (57) ABSTRACT

A spinal rod assembly may be formed by attaching an extension portion onto a spinal rod that extends along a longitudinal axis. The extension portion may include a rod coupler that attaches to the spinal rod with a first coupling that includes a first degree of rotational freedom and a first degree of translational freedom in positioning the rod coupler relative to the spinal rod along the longitudinal axis. The extension portion may further include an extender rod including an elongated rod body that may be secured to the rod coupler using a second coupling that includes at least a second degree of rotational freedom in positioning the extender rod relative to the rod coupler about an axis substantially perpendicular to the longitudinal axis. The extension portion may be assembled in situ to a spinal rod that has been previously secured to vertebral bodies in a patient.

18 Claims, 6 Drawing Sheets

SPINAL ROD EXTENDERS AND METHODS OF USE

CROSS-REFERENCE TO RELATED APPLICATIONS

This application claims priority to and is a continuation of U.S. patent application Ser. No. 11/469,008 filed on Aug. 31, 2006, which is hereby incorporated herein by reference in its entirety.

BACKGROUND

Spinal rods are often used in the surgical treatment of spinal disorders such as degenerative disc disease, disc herniations, scoliosis or other curvature abnormalities, and fractures. Different types of surgical treatments are used. In some cases, spinal fusion is indicated to inhibit relative motion between vertebral bodies. In other cases, dynamic implants are used to preserve motion between vertebral bodies. For either type of surgical treatment, spinal rods may be attached to the exterior of two or more vertebrae, whether it is at a posterior, anterior, or lateral side of the vertebrae. In other embodiments, spinal rods are attached to the vertebrae without the use of dynamic implants or spinal fusion.

Spinal rods may provide a stable, rigid column that encourages bones to fuse after spinal-fusion surgery. Further, the rods may redirect stresses over a wider area away from a damaged or defective region. Also, a rigid rod may restore the spine to its proper alignment. In some cases, a flexible rod may be appropriate. Flexible rods may provide some advantages over rigid rods, such as increasing loading on interbody constructs, decreasing stress transfer to adjacent vertebral elements while bone-graft healing takes place, and generally balancing strength with flexibility.

It is sometimes the case, such as with degenerative diseases, that vertebral levels adjacent to a previously implanted spinal rod may begin to deteriorate. In other cases, such as with spinal correction, a surgeon may elect to insert spinal rods in stages. In either case, revision surgeries may be indicated to secure additional vertebral levels with longer spinal rods. These types of surgeries usually require detachment and removal of the originally implanted rods and insertion of a longer rod into the existing anchors. However, a surgeon may prefer to leave the original implant intact to preserve fusion sites and/or implant geometry. Accordingly, conventional spinal rod systems may not permit extendable attachment of additional spinal rods to previously implanted spinal rods.

SUMMARY

Illustrative embodiments disclosed herein are directed to a spinal rod assembly that may be formed by attaching an extension portion onto a spinal rod that extends along a longitudinal axis. The extension portion may be assembled in situ to a spinal rod that has been previously secured to vertebral bodies in a patient. The extension portion may be assembled to a spinal rod prior to insertion into a patient. For either approach, the extension portion may include a rod coupler that attaches to the spinal rod with a first coupling that includes a first degree of rotational freedom and a first degree of translational freedom in positioning the rod coupler relative to the spinal rod along the longitudinal axis. The rod coupler may include an open channel formed between first and second walls, the channel sized to accept the spinal rod in a lateral direction between the first and second walls. One or both of the walls may include a retainer extending into the channel. The rod coupler may be positioned as desired relative to the spinal rod and secured. The extension portion may further include an extender rod including an elongated rod body that may be secured to the rod coupler using a second coupling that includes at least a second degree of rotational freedom in positioning the extender rod relative to the rod coupler about an axis substantially perpendicular to the longitudinal axis. In one embodiment, the second coupling includes a second degree of translational freedom in establishing an offset of the rod extension relative to the spinal rod.

DETAILED DESCRIPTION

Figure 1:
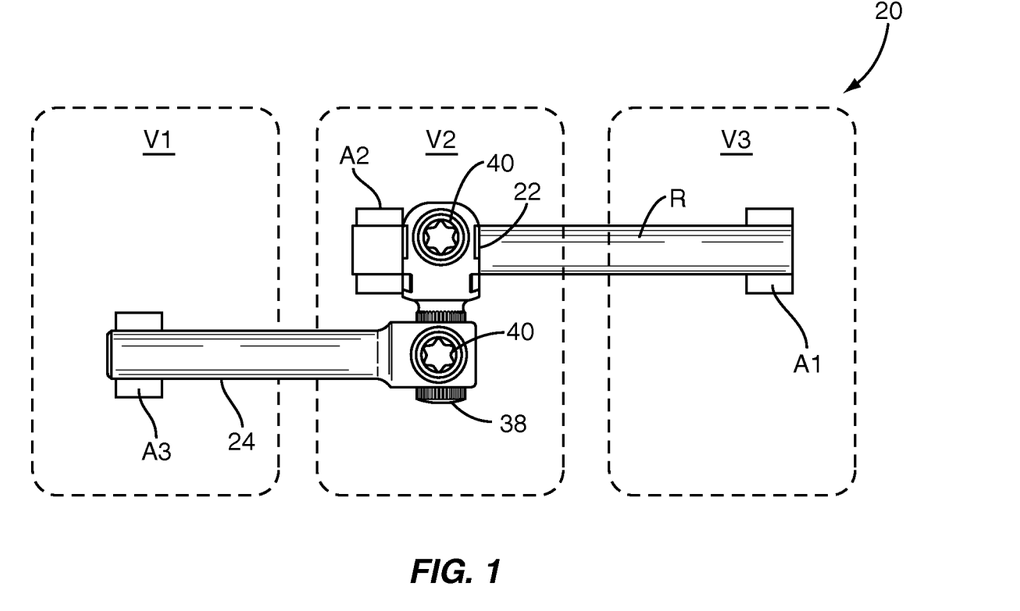
FIG. 1 is a top view of a rod assembly including a rod extender secured to vertebral members according to one embodiment.
Figure 2:
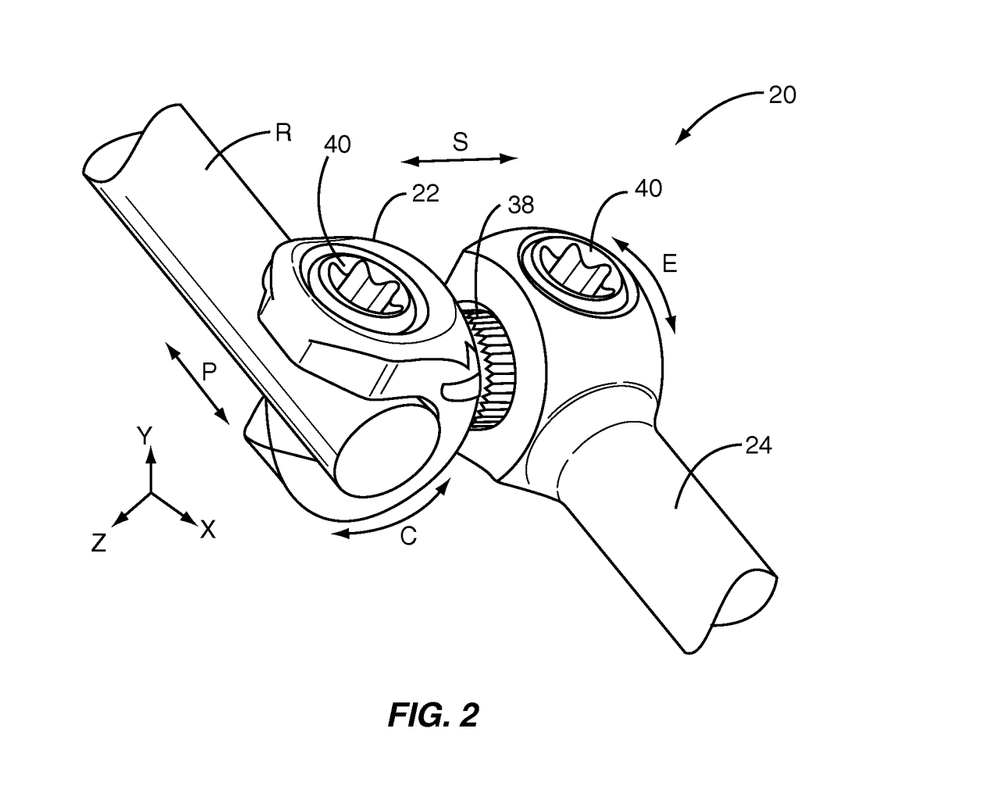
FIG. 2 is a perspective view of a spinal rod extender according to one embodiment.

The various embodiments disclosed herein are directed to spinal rod extenders that permit linking of multiple rod portions, thereby providing an extendable, modular rod system. Generally, the spinal rod extenders may be secured to a conventional rod prior to or after implantation into a patient. A conventional rod may be similar to those used in the CD Horizon® rod systems available from Medtronic, Spinal & Biologics Division in Memphis, Tenn., USA. The rod extenders may be implanted at the same time and in conjunction with a conventional rod. However, the rod extenders also are advantageously attachable to conventional rods that are already secured to vertebral bodies in a patient. Thus, the rod extenders may be implanted at some time after a conventional rod is implanted, such as in a revision procedure. Various embodiments of a spinal rod extender may be implemented in a spinal rod assembly of the type indicated generally by the numeral 20 in FIGS. 1 and 2. Spinal rods assemblies 20 of the type shown may be attached to a spine at various locations, including posterior, lateral, and anterior locations. Spinal rod assemblies 20 may also be attached at various sections of the spine, including the base of the skull and to vertebrae in the cervical, thoracic, lumbar, and sacral regions. The spinal rod assemblies 20 may be secured to the spine using conventionally known attachment anchors A1, A2, A3 such as pedicle screws or other threaded anchors, and other conventionally known hardware, including for example hooks and plates. Accordingly, the spinal rod assemblies 20 may include various lengths, diameters, and configurations. Thus, the illustrations in FIGS. 1 and 2 are provided merely as a representative example of one application of a spinal rod assembly 20. FIG. 1 shows a top view of the spinal rod assembly 20 while FIG. 2 shows a perspective view the spinal rod assembly 20 in which a conventional spinal rod R is attached to extender components, including an extender coupler 22 and an extender rod 24.

In FIG. 1, the spinal rod assembly is shown relative to representative vertebral bodies V1, V2, V3, illustrated simply as dashed blocks. In an exemplary application of the rod assembly 20, the conventional spinal rod R may have been previously implanted into a patient and secured to vertebral bodies V1, V2 using appropriate anchors A1, A2. Various types of anchors, including for example fixed, and multi-axial pedicle screws also available with the CD Horizon® rod system family of devices. At some later point in time, the extender coupler 22 and an extender rod 24 may be added to the existing rod R without having to remove the rod R or detach the anchors A1, A2. Instead, the rod coupler 22 and extender rod 24 are attached to the rod R in situ and the extender rod 24 may be secured to a third vertebral body V3 using a third anchor A3. In an alternative approach, the entire rod assembly 20 may be assembled and secured to the vertebral bodies V1, V2, V3 at substantially the same time.

The extender coupler 22 and extender rod 24 are generally constructed of biocompatible materials. These include metals such as stainless steels, cobalt-chrome, titanium, and shape memory alloys such as nitinol. Non-metallic components, including polymers made from materials such as PEEK and UHMWPE, are also contemplated. Those skilled in the art will comprehend various advantage and characteristics provided by different material choices. Through appropriate material choices, substantially rigid constructs or semi-rigid or flexible constructs may be created.

Figure 3:
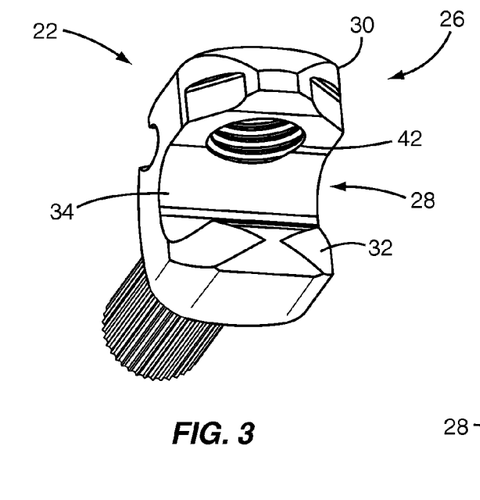
FIG. 3 is a perspective view of a spinal rod extender coupler according to one embodiment.
Figure 4:
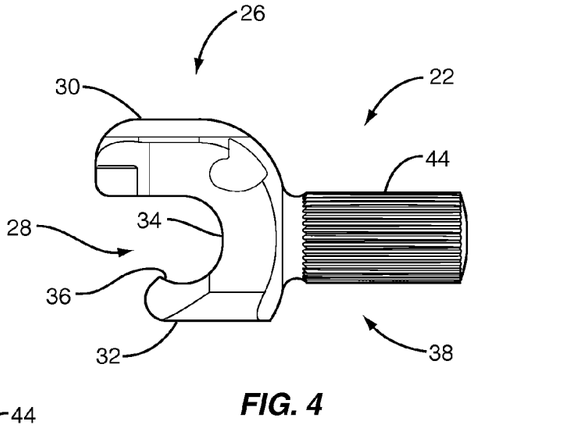
FIG. 4 is a side view of a spinal rod extender coupler according to one embodiment.
Figure 5:
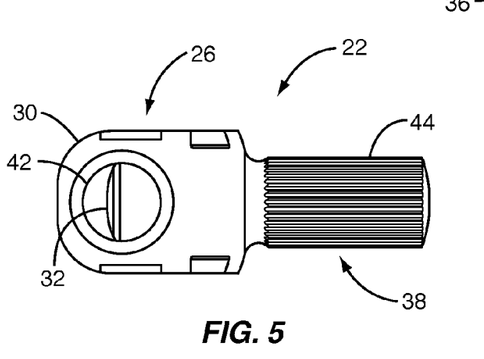
FIG. 5 is a top view of a spinal rod extender coupler according to one embodiment.

A conventional spinal rod R generally includes an elongated body with a circular cross section. However, in the embodiments disclosed herein, non-circular cross sections are equally applicable. Cross section widths between about 3 mm and about 8 mm are known, though other sizes may be used. Regardless of the rod R geometry, the extender coupler 22 includes a receiver section 26 that is configured to accept a rod R. One embodiment of an extender coupler 22 is shown in greater detail in the perspective view provided in FIG. 3. FIG. 4 shows a side view of this same extender coupler 22. FIG. 5 shows a top view of this same extender coupler 22.

In the illustrated embodiment, the receiver section 26 includes a channel 28 that is sized to accept a rod R. The channel 28 is formed between an upper wall 30 and a lower wall 32 and a seating surface 34 extending therebetween. In one embodiment, the upper wall 30 is longer than the lower wall 32. In another embodiment, the upper and lower walls 30, 32 include substantially similar lengths. Similarly, the lower wall 32 may be longer than the upper wall 30. In any event, the lower wall 32 may include a retention feature 36 to retain a rod R that is inserted into the channel 28. The retention feature 36 is formed as a protrusion that extends slightly into the channel 28 towards the upper wall 30. Once a rod R is secured in the channel 28, the retention feature 36 prevents the rod R from dislocating laterally out of the channel 28. Further, in the embodiment shown, the channel 28 is open laterally, with a coupler post 38 extending laterally in a direction opposite the open end of the channel 28. In one embodiment, the channel 28 may be open towards the top or bottom of the extender coupler 22. There is no express requirement that the channel 28 and coupler post 38 extend laterally in opposite directions.

Figure 6:
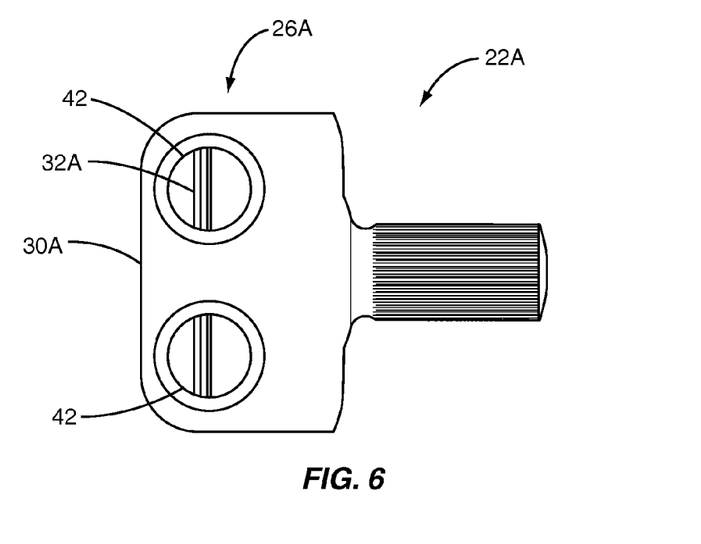
FIG. 6 is a top view of a spinal rod extender coupler according to one embodiment.

A rod R may be secured within the channel 28 with a retainer 40 as shown in FIGS. 1 and 2. The retainer 40 may be implemented as a setscrew as shown, though other types of fasteners may be used. Exemplary retainers 40 may include pins, plugs, dowels, quarter-turn fasteners, clips, rings, and other fasteners conceivable by those skilled in the art. A setscrew retainer 40 as shown may provide substantial clamping forces to secure a rod R within the channel 28. In the embodiment shown, the setscrew retainer 40 is insertable into a threaded aperture 42 in the upper wall 30 of the receiver section 26. In one embodiment, the receiver section 26 includes a single threaded aperture 42 to receive a setscrew retainer 40. In other embodiments, such as that illustrated in FIG. 6, the receiver section 26 includes multiple threaded apertures 42 to receive multiple setscrew retainers 40 for additional securing to a rod R. The extender coupler 22 can be inserted onto and secured to the rod R by clamping the rod R within the channel 28 using the retainer 40.

FIG. 2 shows that there is some flexibility in attaching the extender coupler 22 to the rod R. Specifically, FIG. 2 shows two sets of arrows labeled C and P, respectively. These arrows are shown relative to an X-Y-Z coordinate system. The rod R is generally aligned with the X-axis. It is generally known that rods R may be bent to conform to a patient anatomy or to achieve a desired spinal alignment. However, for the sake of description and simplicity, the rod R shown in FIGS. 1 and 2 is depicted as extending in a straight line. For a curved rod R, the X-Y-Z coordinate system remains relevant by aligning the X-axis of the coordinate system with the longitudinal axis of the rod R at the point where the extender coupler 22 is attached to the rod R. With either convention, the extender coupler 22 may be positioned at various locations along the longitudinal length of the rod R. This flexibility is identified by the arrows labeled P, which extend along the X-axis or along the rod R axis. In addition, the extender coupler 22 may be positioned at various rotatable orientations identified by the arrows labeled C, which rotate about the X-axis or about the rod R axis. That is, the extender coupler 22 may be rotated and secured at various locations (limited potentially by anatomy) within the Y-Z plane. These arrows represent a single degree of translational freedom and a single degree of rotational freedom in positioning the extender coupler 22 to a rod R.

Figure 7:
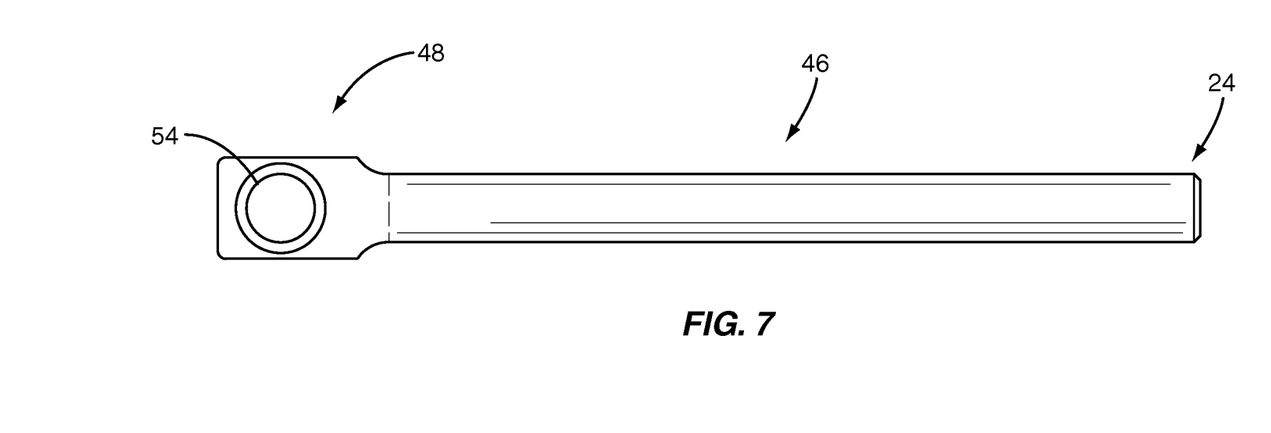
FIG. 7 is a top view of an extender rod according to one embodiment.
Figure 8:
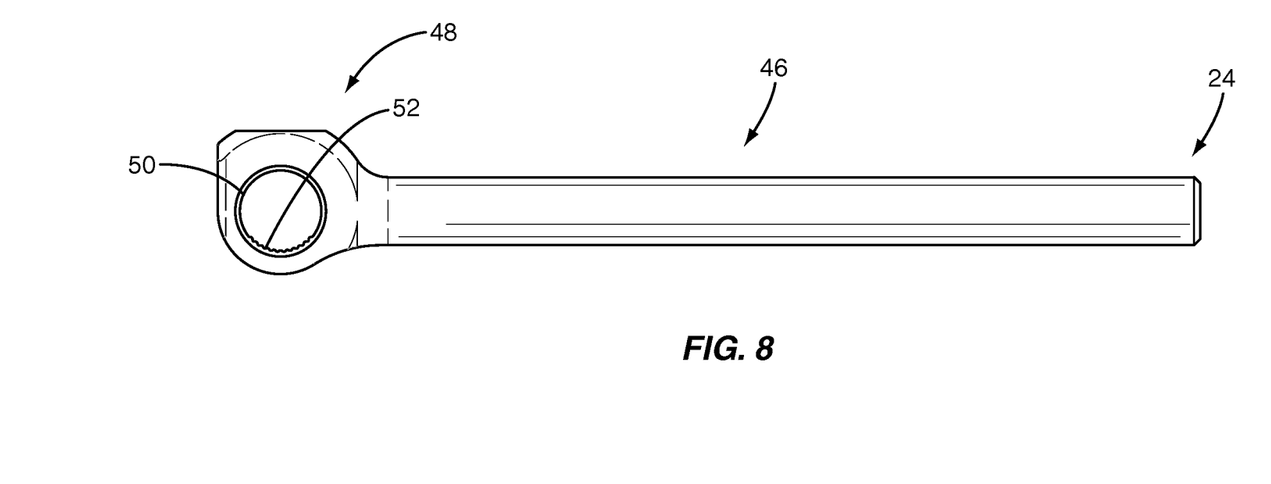
FIG. 8 is a perspective view of an extender rod according to one embodiment.

As indicated, the coupler post 38 extends from the receiver section 26. In one embodiment, the coupler post 38 includes splines 44 extending longitudinally about the exterior surface of the coupler post 38. The extender rod 24 is attachable to the coupler post 38 in the manner illustrated in FIGS. 1 and 2. FIGS. 7 and 8 respectively illustrate top and side views of an extender rod 24 according to one embodiment. The extender rod 24 includes an elongated rod portion 46 that is formed substantially similar to conventional rods R. That is, the rod portion 46 includes a circular cross section with a diameter between about 3 mm and about 8 mm. Of course, different diameters and different materials will have different flexural and torsional rigidities. Those skilled in the art will comprehend suitable diameters to achieve desired rod strengths. In other embodiments, the rod portion 46 may include non-circular and even asymmetric cross sections.

The extender rod 24 includes an attachment portion 48 that is disposed at one end of the extender rod 24 in the embodiment shown. In the embodiment shown, the attachment portion 48 is enlarged compared to the rod portion 46. However, depending on the size of the rod portion 46 and the coupler post 38, the attachment portion 48 may include a similar size and width as the rod portion 46. The attachment portion 48 includes an aperture 50 that engages the coupler post 38 of the extender coupler 22. That is, the aperture 50 is sized to receive the coupler post 38. The aperture 50 may extend through the attachment portion 48 or may extend a predetermined depth. The aperture 50 may include one or more protrusions 52, including for example a plurality of splines, that engage correspondingly-configured splines 44 on the coupler post 38. The aperture 50 may include a slightly larger width than that of the coupler post 38. In this manner, the coupler post 38 may be rotated (as shown by the arrows labeled E in FIG. 2) within the aperture 50 to achieve a desired orientation. Further, the extender rod 24 may be secured at varying offset distances from the rod R as indicated by the arrow S. The amount of adjustment in this offset direction S is limited by the length of the coupler post 38.

Thus, combined with the permissible motion depicted by arrows P and C in FIG. 2, the extender rod system 20 permits two-degrees of rotational freedom and two-degrees of translational freedom in assembling the rod extender components 22, 24 to the rod R. Then, the coupler post 38 may be secured within the aperture 50 with a retainer 40 as shown in FIGS. 1 and 2. As suggested above, the retainer 40 may be implemented as a setscrew as shown, though other types of fasteners may be used. Exemplary retainers 40 may include pins, plugs, dowels, quarter-turn fasteners, clips, rings, and other fasteners conceivable by those skilled in the art. A setscrew retainer 40 as shown may provide substantial clamping forces to secure the coupler post 38 within the aperture 50. Furthermore, the splines 44, 52 cooperate to prevent rotation of the extender rod 24 relative to the extender coupler 22 after the retainer 40 is inserted. In the embodiment shown, the setscrew retainer 40 is insertable into a threaded aperture 54 in the attachment portion 48. In one embodiment, the attachment portion 48 includes a single threaded aperture 54 to receive a setscrew retainer 40. In other unillustrated embodiments, the attachment portion 48 includes multiple threaded apertures 54 to receive multiple setscrew retainers 40.

Figure 9:
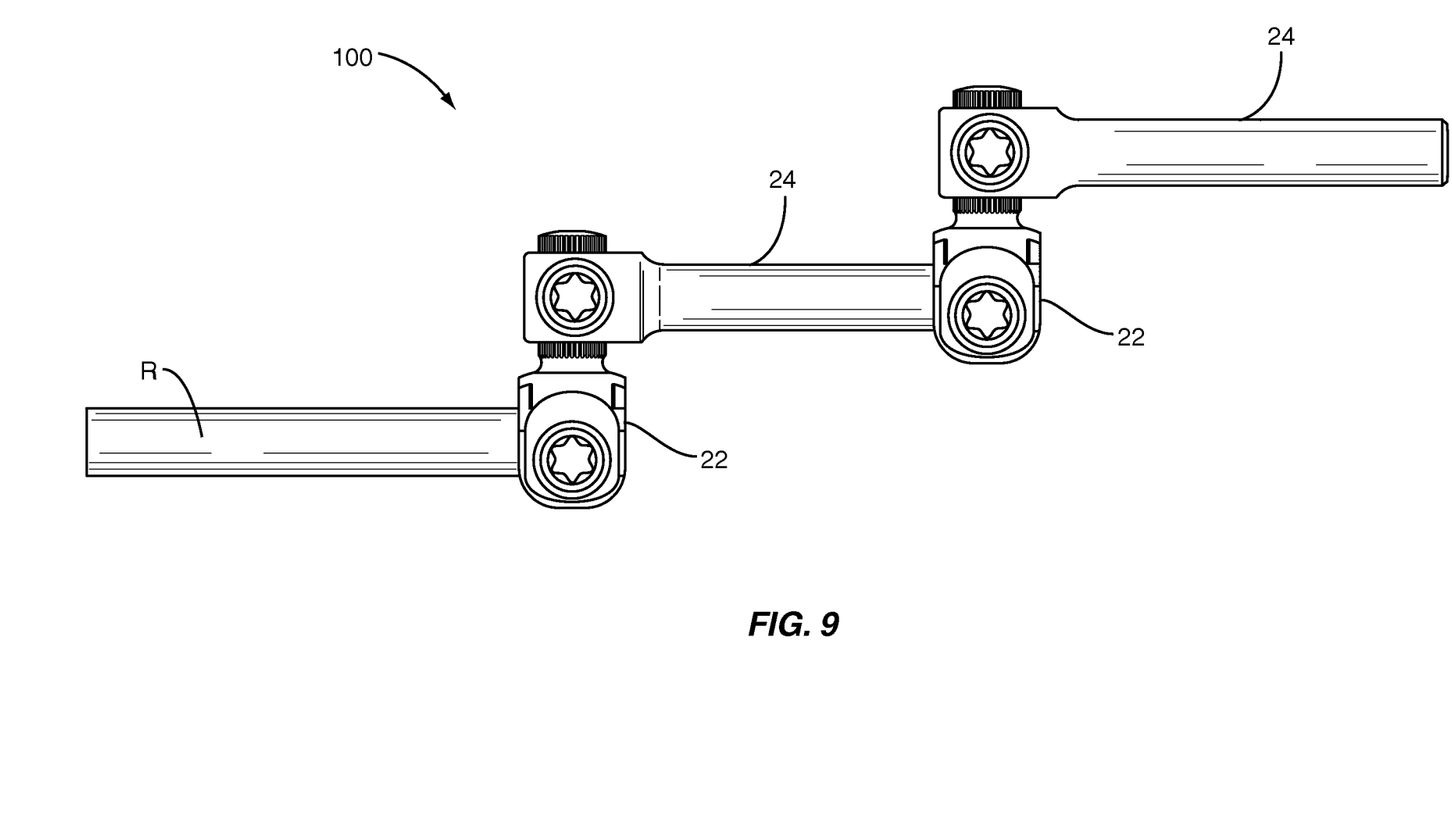
FIG. 9 is a top view of a spinal rod extender according to one embodiment.

FIGS. 1 and 2 depicted a rod assembly 20, including a single extender coupler 22 and a single extender rod 24 coupled to a conventional rod R. Since the extender rod 24 includes a rod portion 46 formed similar to a conventional rod R, a rod system 100 shown in FIG. 9 may be formed using multiple extender couplers 22 and extender rods 24. In the illustrated example, the rod system 100 includes a conventional rod R and a linked rod extender including two extender couplers 22 and two extender rods 24. Additional extender couplers 22 and extender rods 24 may be added as desired to achieve a desired overall length.

Figure 10:
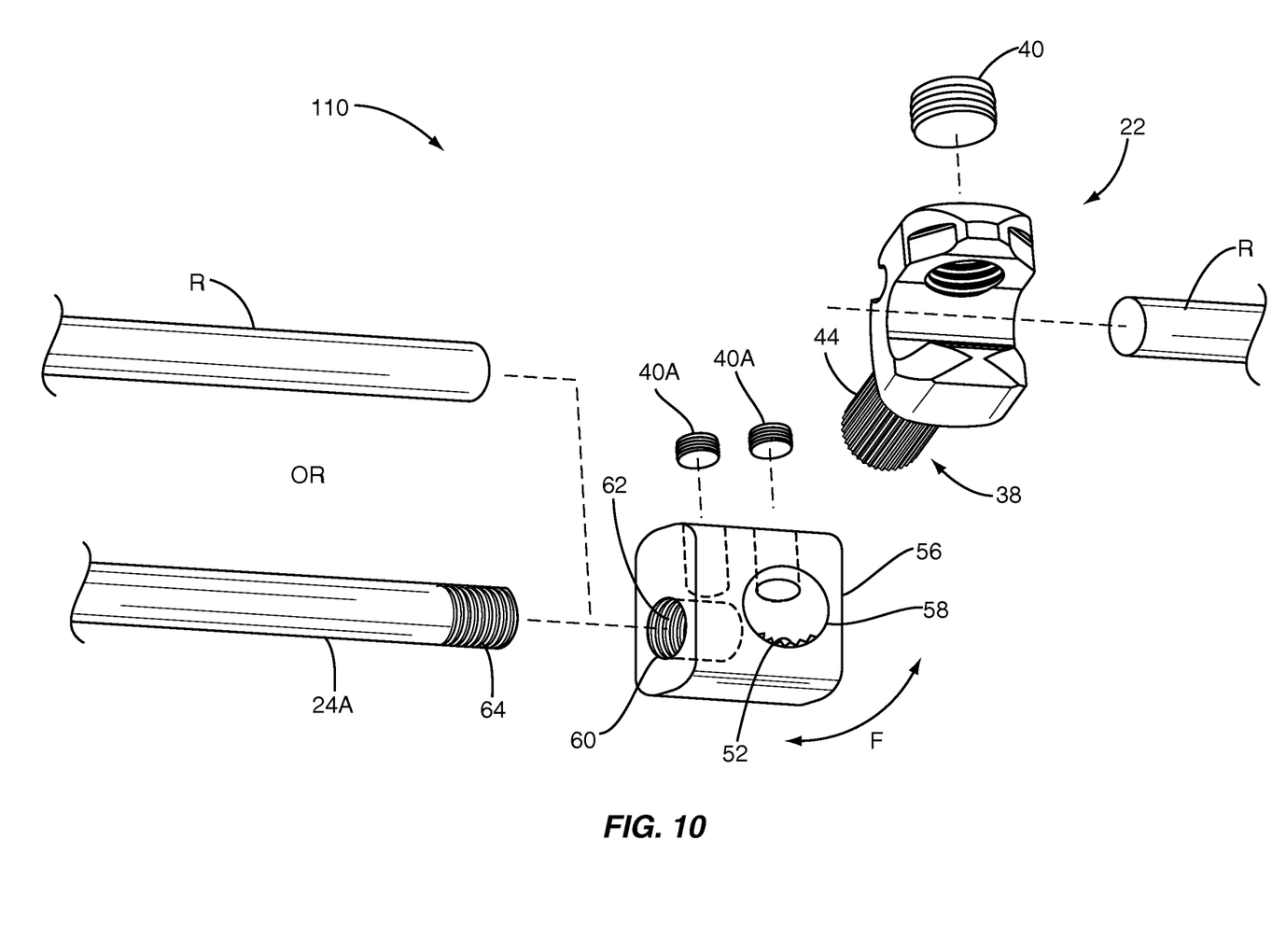
FIG. 10 is a perspective view of an exploded spinal rod extender assembly according to one embodiment.

FIG. 10 depicts an embodiment of a rod extender system 110 that uses an extender coupler 22 for attachment to a conventional rod R as described above. In the present embodiment, an extender rod 24A is attached to the extender coupler 22 via a coupling block 56. Functionally, the coupling block 56 couples the extender rod 24A to the extender coupler 22. Further, the coupling block 56 is rotatable in the direction of arrows F thereby providing flexibility in angling the extender rod 24A relative to the conventional rod R to which the extender coupler 22 is attached. Specific features of the exemplary coupling block 56 are more clearly visible in the front and side views provided in FIGS. 11 and 12. The illustrated coupling block 56 is generally rectangular in form, but other shapes are certainly permissible. For example, elliptical, oblong, or teardrop shapes may be used. The coupling block 56 includes an aperture 58 that engages the coupler post 38 of the extender coupler 22. That is, the aperture 58 is sized to receive the coupler post 38. The aperture 58 may extend through the coupling block 56 or may extend a predetermined depth. The aperture 58 may include one or more protrusions 52, including for example a plurality of splines, that engage correspondingly-configured splines 44 on the coupler post 38. The aperture 58 may include a slightly larger width than that of the coupler post 38. In this manner, the coupler post 38 may be rotated (as shown by the arrows labeled F) within the aperture 58 to achieve a desired orientation. Then, the coupler post 38 may be secured within the aperture 58 with a retainer 40A such as a setscrew or other member as described herein.

Figure 11:
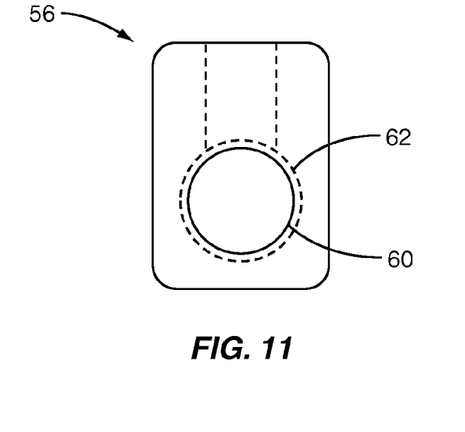
FIG. 11 is a front view of a spinal rod extender coupling block according to one embodiment.
Figure 12:
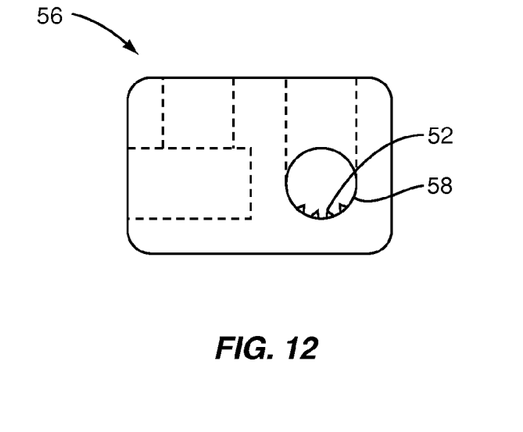
FIG. 12 is a side view of a spinal rod extender coupling block according to one embodiment.

The coupling block 56 further includes an aperture 60 that engages the extender rod 24A. That is, the aperture 60 is sized to receive an end of the extender rod 24A. In the embodiment shown, the aperture 60 is oriented to face a direction that is substantially perpendicular to the extender post aperture 58. In other embodiments, the extender rod aperture 60 may face a direction other than substantially perpendicular to the extender post aperture 58. The aperture 60 may extend through the coupling block 56 or may extend a predetermined depth. The aperture 60 may include threads 62 that engage correspondingly-configured threads 64 on the extender rod 24A. Accordingly, the extender rod 24A may be threaded into the aperture 60 in the coupling block 56. Then, the extender rod 24A may be secured using a retainer 40A such as a setscrew or other member as described herein. In an alternative implementation, a conventional rod R may be coupled to the coupling block 56 instead of the illustrated extender rod 24A. The rod R may be inserted into the aperture 60 (which may or may not include threads 62 in the coupling block 56. Then, the rod R may be secured using a retainer 40A such as a setscrew or other member as described herein.

Figure 13:
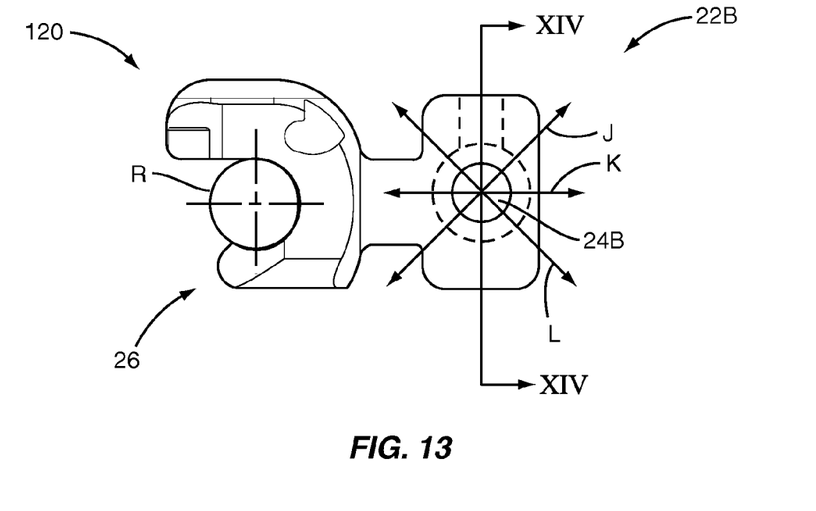
FIG. 13 is an axial view of a spinal rod extender assembly according to one embodiment.
Figure 14:
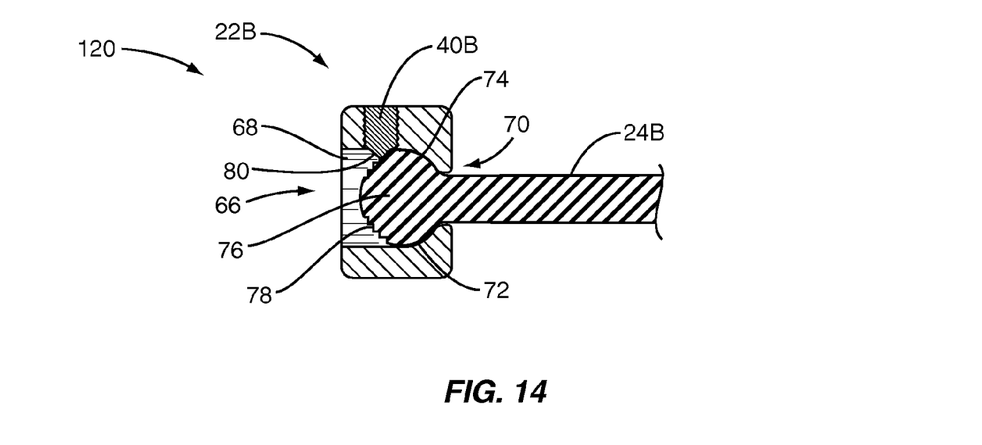
FIG. 14 is side section view of a spinal rod extender assembly according to one embodiment.

FIGS. 13 and 14 illustrate an embodiment of a rod extender system 120 in which an extender coupler 22B engages an extender rod 24B. The extender coupler 22B includes a receiver section 26 that is configured to accept a rod R as described above. The extender coupler 22B includes an aperture 66 that extends between an enlarged insertion end 68 and a narrowed bottom end 70. Between these ends 68, 70, the aperture 66 includes a spherical surface 72 that is formed to substantially match and engage a spherical surface 74 of an enlarged end 76 of the extender rod 24B. Thus, the spherical surface 74 at the enlarged end 76 of the extender rod 24B and the spherical surface 72 of the aperture 66 form a ball and socket joint that permits poly-axial movement of the extender rod 24B relative to the rod R. The enlarged end 76 of the extender rod 24B may include ridges 78 that can be engaged by a tip 78 of a setscrew retainer 40B. The tip 78 of the setscrew retainer 40B may be pointed as shown. In other embodiments, the tip 78 may be spherical, cupped, conical, or other shapes that would occur to one skilled in the art. Furthermore, the tip 78 may be deformable and include relatively soft materials, including for example metal alloys including silver or polymers including nylon that are deformable to further engage and secure the enlarged end 76 of the extender rod 24B within the aperture 66 in the extender coupler 22B.

The inclusion of a ball-and-socket coupling between the extender rod 24B and the extender coupler 22B provides additional degrees of rotational freedom over previously described embodiments (at the expense of losing the translational freedom identified by the arrow labeled S in FIG. 2). Specifically, the extender rod 24B is able to rotate or pivot about a plurality of axes as represented by the arrows labeled J, K, L in FIG. 13. Notably, these axes are substantially perpendicular to the longitudinal axis of the rod R at the point where the extender coupler 22B is coupled to the rod R.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For example, embodiments described above have contemplated an extender post on an extender coupler that engages an aperture in an extender rod or coupling block. In other embodiments, the post may be disposed on the coupling block or extender rod while the aperture is disposed on the extender coupler. Thus, the coupling block or the extender rod may be inserted into the extender coupler in contrast with the illustrated configurations. The present embodiments are, therefore, to be considered in all respects as illustrative and not restrictive, and all changes coming within the meaning and equivalency range of the appended claims are intended to be embraced therein.

What is claimed is:

1. A method of supporting vertebral members, the method comprising the steps of:
    coupling a rod coupler to an elongated spinal rod extending along a longitudinal axis, the rod being previously secured in proximity to the vertebral members, the rod coupler including a channel formed between first and second walls, the channel sized to accept the spinal rod in a lateral direction between the first and second walls;
    adjusting the rod coupler along the longitudinal axis to a desired position on the spinal rod;
    adjusting the rod coupler about the longitudinal axis to a desired angular position about the spinal rod;
    securing the rod coupler to the spinal rod;
    coupling an extender rod including an elongated rod body to the rod coupler such that the rod body extends parallel to the longitudinal axis;
    adjusting the extender rod about an axis extending transverse to the longitudinal axis to a desired angular position relative to the rod coupler;
    securing the extender rod to the rod coupler; and
    securing the rod body to a vertebral body.

2. The method of claim 1 wherein the step of securing the rod coupler to the spinal rod comprises threading a setscrew through the first wall and into contact with the spinal rod contained within the channel.

3. The method of claim 1 wherein the step of adjusting the extender rod about an axis extending transverse to the longitudinal axis to a desired angular position relative to the rod coupler comprises rotating an aperture formed at an end of the extender rod around a post formed into the coupler.

4. The method of claim 3 wherein the post extends perpendicular to the longitudinal axis and includes splines extending about an exterior of the post and the aperture includes a plurality of splines, and wherein rotating the aperture around the post comprises engaging the splines on the post with the splines of the aperture.

5. The method of claim 1 wherein the step of adjusting the extender rod about an axis extending transverse to the longitudinal axis to a desired angular position relative to the rod coupler comprises pivoting a spherically-shaped head formed at an end of the extender rod relative to a spherically-shaped recess formed into the coupler.

6. The method of claim 1 wherein the step of securing the extender rod to the rod coupler comprises threading a setscrew into contact with the extender rod and the rod coupler.

7. The method of claim 1 further comprising adjusting the extender rod along the axis extending transverse to the longitudinal axis to a desired offset position relative to the spinal rod prior to the step of securing the extender rod to the rod coupler.

8. The method of claim 7 wherein the step of adjusting the extender rod along the axis extending transverse to the longitudinal axis to a desired offset position relative to the spinal rod comprises adjusting the position of a post formed into the coupler within an aperture formed at an end of the extender rod.

9. The method of claim 1 wherein the first and second walls are spaced apart side walls, the channel being formed by the first and second walls and a back wall, the first and second walls extending away from the back wall and terminating at ends.

10. The method of claim 1 wherein the first and second walls are spaced apart side walls, the channel being formed by the first and second walls and a back wall, the first and second walls extending away from the back wall and terminating at ends, and wherein the channel has an open side opposite the back wall and between the ends of the first and second walls.

11. The method of claim 1 wherein the step of securing the extender rod to the rod coupler comprises threading a threaded setscrew into a threaded aperture in the extender rod that extends perpendicular to the longitudinal axis.

12. The method of claim 1 wherein the rod coupler comprises a post extending perpendicular to the longitudinal axis and an aperture extending through the first wall, and wherein the step of securing the rod coupler to the spinal rod comprises threading a setscrew into the aperture such that the setscrew engages the spinal rod.

13. A method of supporting vertebral members, the method comprising the steps of:
    coupling a rod coupler to an elongated spinal rod extending along a longitudinal axis using a first coupling that includes a first degree of rotational freedom and a first degree of translational freedom in positioning the rod coupler relative to the spinal rod along the longitudinal axis;
    securing the rod coupler to the spinal rod at a desired first translational position and a first rotational position;
    coupling an extender rod including an elongated rod body to the rod coupler such that the rod body extends parallel to the longitudinal axis using a second coupling that includes at least a second degree of rotational freedom in positioning the extender rod relative to the rod coupler about an axis substantially perpendicular to the longitudinal axis;
    securing the extender rod to the rod coupler at a second rotational position by threading a setscrew into contact with the extender rod and the rod coupler; and
    securing the elongated rod body to a vertebral body.

14. The method of claim 13 wherein the step of coupling a rod coupler to an elongated spinal rod comprises laterally inserting the rod coupler including an open channel formed between first and second walls around the spinal rod with the rod positioned within the channel.

15. The method of claim 13 wherein the step of coupling an extender rod including an elongated rod body to the rod coupler using a second coupling comprises rotating an aperture formed at an end of the extender rod around a post formed into the coupler.

16. The method of claim 13 wherein the step of coupling an extender rod including an elongated rod body to the rod coupler using a second coupling comprises inserting a spherically-shaped head formed at an end of the extender rod into a spherically-shaped recess formed into the coupler.

17. The method of claim 13 wherein the second coupling further includes a second degree of translational freedom in positioning the extender rod relative to the rod coupler along the axis substantially perpendicular to the longitudinal axis and further comprising adjusting the extender rod along the axis extending transverse to the longitudinal axis to a desired offset position relative to the spinal rod prior to the step of securing the extender rod to the rod coupler.

18. The method of claim 17 wherein the step of adjusting the extender rod along the axis extending transverse to the longitudinal axis to a desired offset position relative to the spinal rod comprises adjusting the position of a post formed into the rod coupler within an aperture formed at an end of the extender rod.

\* \* \* \* \*